US005553606A

United States Patent [19]

Chen

[11] Patent Number: 5,553,606

[45] Date of Patent: Sep. 10, 1996

[54] SNORKEL FACE MASK HAVING A LIGHT DEVICE

[76] Inventor: Johson Chen, Floor 7, No. 85, Li-Kung Road, Taiping Hsiang, Tatchung County, Taiwan

[21] Appl. No.: 553,855

[22] Filed: Nov. 6, 1995

[51] Int. Cl.[6] ................................ A61B 1/06; F21L 15/14

[52] U.S. Cl. ................................ 128/202.13; 128/201.11; 128/201.12; 128/206.12; 128/206.28; 362/105

[58] Field of Search .......................... 128/201.11, 201.12, 128/202.13, 206.12, 206.28, 206.29; 362/103, 105, 106

[56] References Cited

U.S. PATENT DOCUMENTS

| | | | |
|---|---|---|---|
| 933,499 | 9/1909 | Taylor | 362/105 |
| 994,094 | 5/1911 | Eaton | 362/105 |
| 1,019,895 | 3/1912 | Hays et al. | 362/105 |
| 1,252,989 | 6/1918 | Ballard | 362/105 |
| 1,294,752 | 2/1919 | Ballard | 362/103 |
| 1,305,852 | 6/1919 | Widmer | 362/105 |
| 1,327,479 | 1/1920 | Jones | 362/1 OS |
| 1,559,191 | 3/1925 | Smith | 362/105 |
| 1,904,902 | 8/1930 | Pratt | 362/105 |
| 1,925,593 | 9/1933 | Long | 362/105 |
| 1,930,620 | 2/1933 | Loveen | 362/105 |
| 2,176,789 | 10/1939 | Capitani | 362/105 |
| 2,289,488 | 7/1942 | Dritsas | 362/105 |
| 2,517,422 | 8/1950 | Gellman | 362/105 |
| 3,008,040 | 11/1961 | Moore | 362/105 |
| 3,069,538 | 12/1962 | Hobson | 362/105 |
| 3,892,234 | 7/1975 | Jones | 128/202.13 |
| 3,912,919 | 10/1975 | Eriksson | 362/105 |
| 3,951,139 | 4/1976 | Kloots | 362/105 |
| 4,090,232 | 5/1978 | Golden | 362/105 |
| 4,631,645 | 12/1986 | Lenart | 362/105 |
| 4,638,410 | 1/1987 | Barker | 128/201.11 |
| 4,998,187 | 5/1991 | Herrick | 362/105 |
| 5,339,464 | 8/1994 | Dor | 2/6.2 |
| 5,420,828 | 5/1995 | Geiger | 367/131 |

*Primary Examiner*—Edgar S. Burr
*Assistant Examiner*—V. Srivastava
*Attorney, Agent, or Firm*—Charles E. Esq. Baxley

[57] ABSTRACT

A face mask for a snorkel device includes a beam engaged on the upper portion of the face mask for securing a light device. The beam includes a cavity formed in the middle portion. A retaining member has an upper leg engaged in the cavity and has a hook formed in the lower leg for engaging with the center portion of the face mask so as to be secured onto the face mask. A light device includes a housing pivotally coupled to the beam for lighting purposes and includes a battery and a socket engaged in the housing and includes a lamp means engaged with the socket. The light device can be easily secured to the face mask such that the divers need not carry the light device with their hands.

4 Claims, 3 Drawing Sheets

SNORKEL FACE MASK HAVING A LIGHT DEVICE

BACKGROUND OF THE INVENTION

1. Field of the Invention

The present invention relates to a face mask, and more particularly to a face mask of a snorkel assembly having a light device.

2. Description of the Prior Art

Typical face masks for snorkel assemblies are necessary equipments provided for engaging with the eye portions of the divers. Typically, divers have to carry a primary oxygen device, an auxiliary oxygen device, a primary light device and an auxiliary light device with them. However, it will be inconvenient to carry such a lot of equipments with the divers.

The present invention has arisen to mitigate and/or obviate the afore-described disadvantages of the conventional snorkel assemblies.

SUMMARY OF THE INVENTION

The primary objective of the present invention is to provide a face mask for a snorkel assembly, in which a light device is secured to the face mask for providing an auxiliary light device to the divers.

In accordance with one aspect of the invention, there is provided a face mask for a snorkel device, the face mask comprises an upper portion and a center portion, and the face mask comprises a beam engaged on the upper portion of the face mask and including a middle portion having a cavity formed therein and including two end portions each having an extension extended therefrom for securing to the face mask, a retaining member including an upper leg engaged in the cavity of the beam and including a lower leg having a hook means formed thereon for engaging with the center portion of the face mask so as to be secured onto the face mask, means for securing the upper leg to the beam so as to secure the beam to the face mask, and a light means secured to the beam for lighting purposes.

The beam includes a pair of lugs extended from the middle portion thereof, a bolt means engaged with the lugs, and the light means includes a housing having a projection extended downward therefrom for engaging with the bolt means so as to be secured to the beam.

The housing includes a hollow interior and includes at least one battery and a socket engaged in the hollow interior of the housing and includes a lamp means engaged with the socket, and includes a parabolic reflector engaged in the housing, the parabolic reflector includes a center hole for engaging with the lamp means, and the housing includes a switch means engaged therein for controlling the lamp means.

A pair of clamping straps are secured to the extensions for securing to the face mask so as to secure the beam to the face mask.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
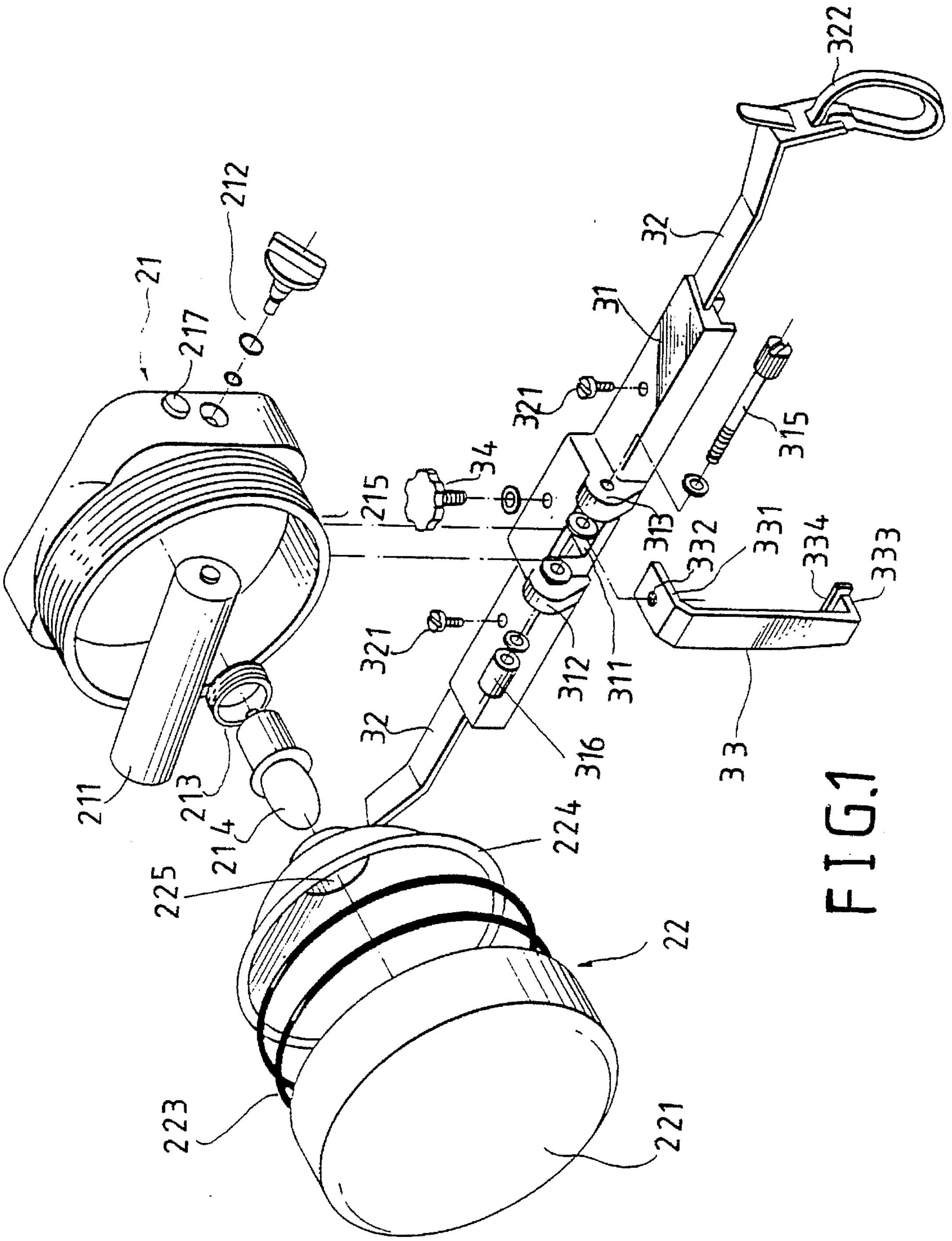
FIG. 1 is an exploded view of a face mask having a light device in accordance with the present invention.
Figure 2:
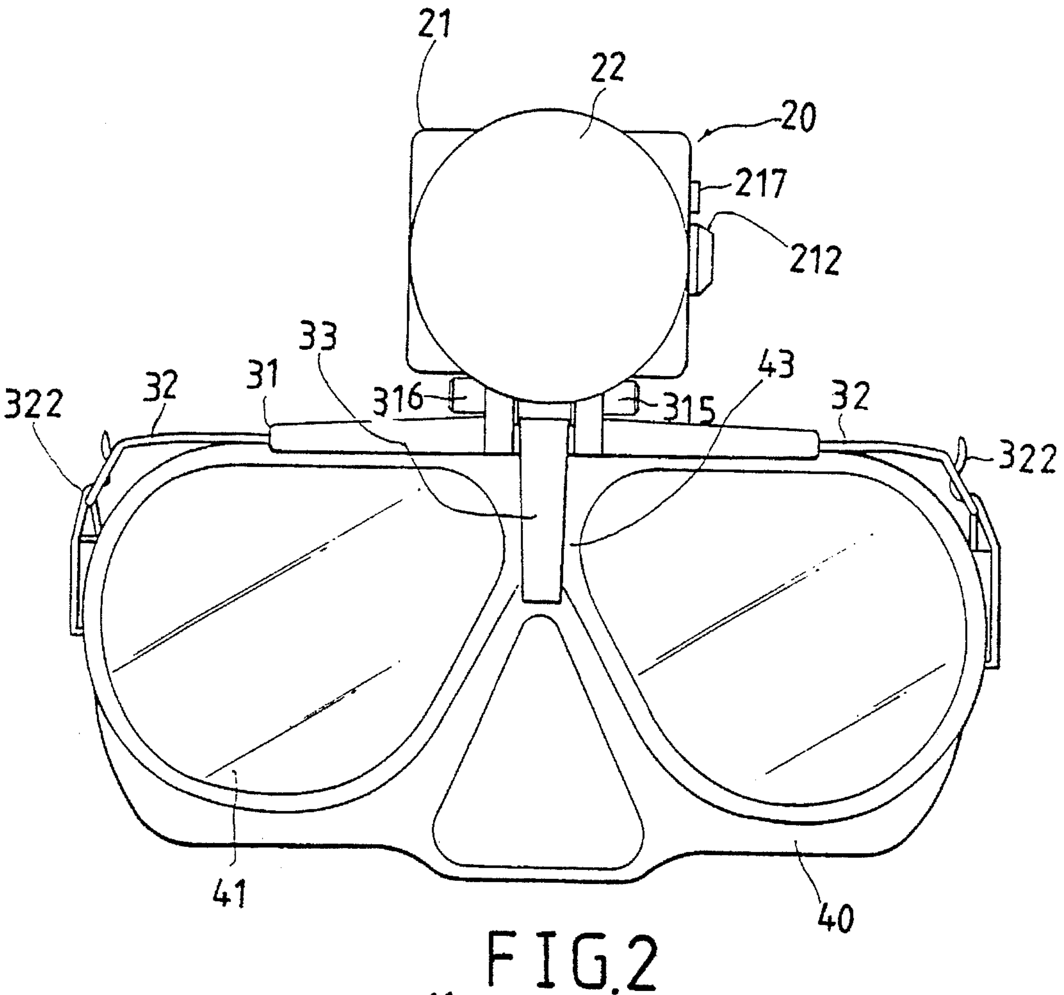
FIG. 2 is a front view of the face mask.
Figure 3:
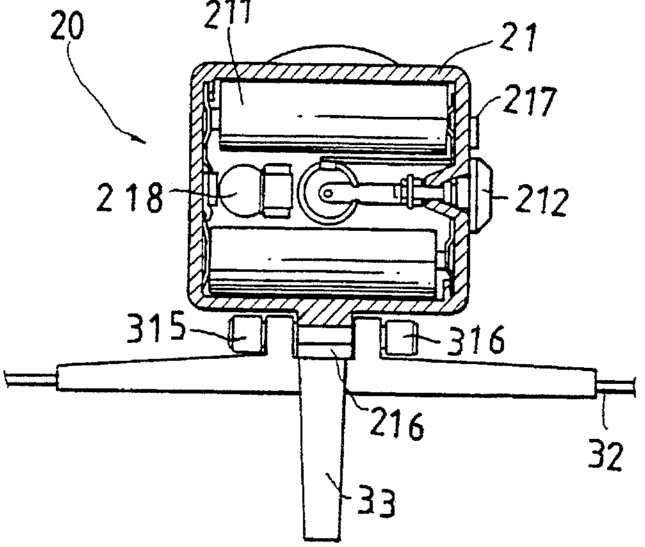
FIG. 3 is a partial cross sectional view of the face mask for showing the interior of the light device.

Referring to FIGS. 1 to 3, a face mask in accordance with the present invention is provided for a snorkel assembly and comprises a light device secured thereto for providing an auxiliary light device to the divers. The face mask 40 includes center portion 43 formed in the center of the face portion 41 and includes a beam 31 having a pair of extensions 32 extended from the end portions thereof and having a cavity 311 formed in the front and middle portion thereof and having a pair of lugs 312 extended therefrom for engaging with a bolt 315 to which a nut 316 is threaded. Two screws 321 are threadedly engaged with the beam 31 so as to secure the extensions 32 to the beam 31. Two clamping straps 322 are secured to the extensions 32 for securing the extensions 32 to the face mask 40. A C-shaped retaining member 33 includes an upper leg 331 engaged in the cavity 311 and having a screw hole 332 formed therein, and includes a lower leg 333 having a hook 334 formed thereon for engaging with the center portion 43 of the face mask 40. A fastening screw 34 is threaded to the middle portion of the beam 31 and is threaded with the screw hole 332 of the retaining member 33 so as to solidly secure the retaining member 33 to the beam 31.

Figure 5:
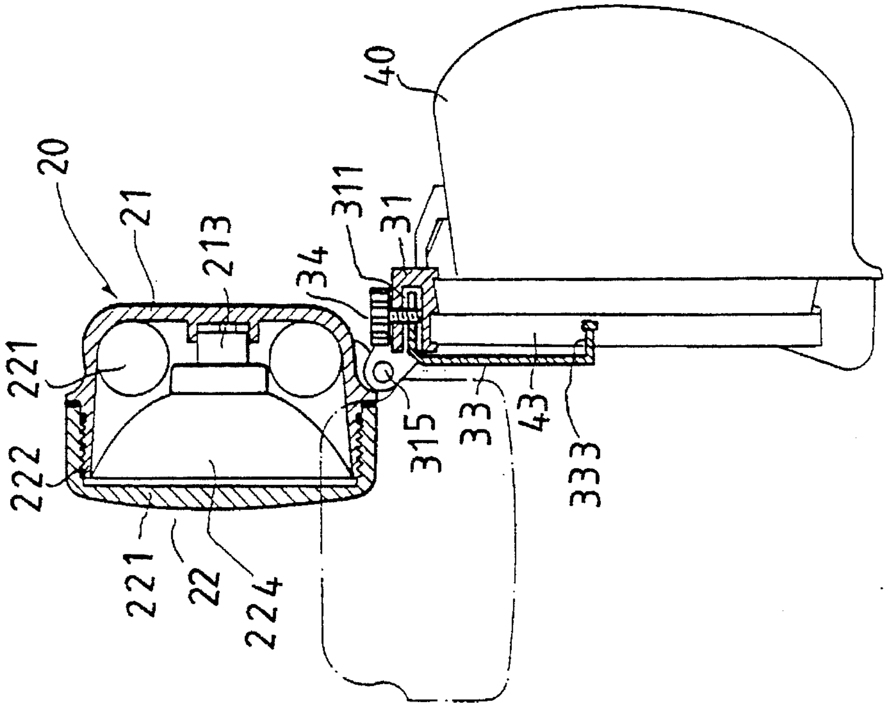
FIG. 5 is a partial cross sectional view of the face mask for showing the interior of the light device.
Figure 4:
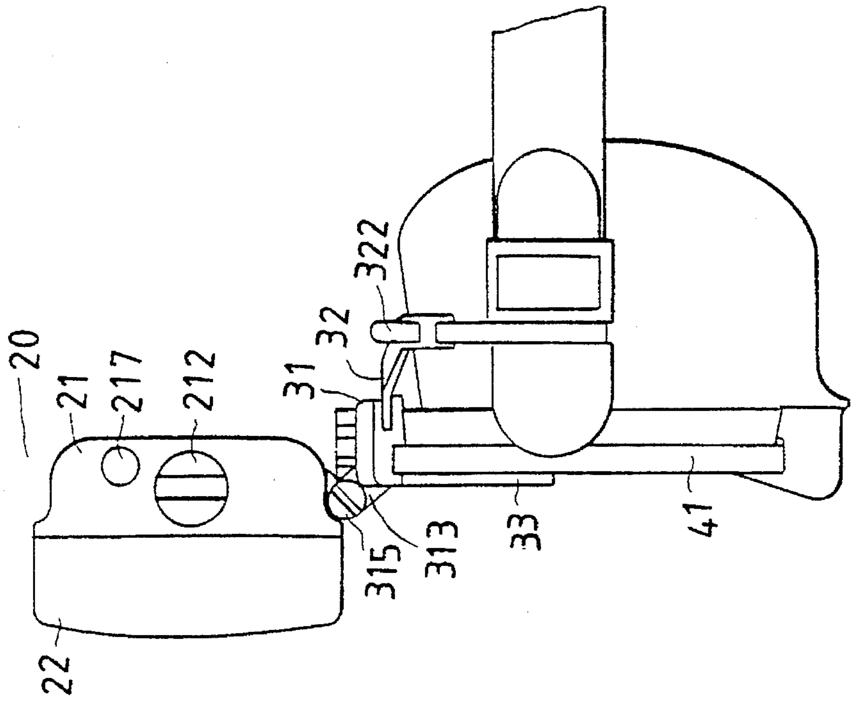
FIG. 4 is a side view of the face mask.

A light device 20 includes a housing 21 having a hollow interior for receiving batteries 211 therein and for receiving a socket 213 therein. A lamp 214 is engaged with the socket 213. A switch 212 is coupled to the housing 21 for switching the lamp 214 on and off. A spare lamp 218 is engaged in the housing 21. The housing 21 further includes a socket 217 provided therein for coupling to an electric source by a connecting wire. The housing 21 includes an outer thread 215 formed thereon and includes a projection 216 extended downward for engaging with the bolt 315 (FIG. 3) such that the housing 21 may be pivotally coupled to the beam 31. A cap 22 includes an inner thread 222 (FIG. 5) formed therein for engaging with the outer thread 215 of the housing 21 so as to be secured to the housing 21. The cup 22 includes a transparent disc 221 secured in the front portion and includes a parabolic reflector 224 engaged therein. The reflector 224 includes an orifice 225 formed therein for engaging with the lamp 214. One or more sealing rings 223 are engaged between the cap 22 and the housing 21 so as to make a water tight seal therebetween.

It is to be noted that the light device 20 may be easily and pivotally secured to the beam 31 by the bolt 315 and may be adjusted to suitable angular positions before the bolt 315 is secured in place. The beam 31 may also be easily secured to the face mask 40 by the retaining member 33 and the clamping straps 322. The divers need not carry the light device with their hands such that the light device can be easily carried with the divers. The beam 31 and the light device 20 may thus be easily secured to any conventional face masks 40 of snorkel devices.

Accordingly, the face mask in accordance with the present invention includes a light device that may be easily secured to the face mask.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A face mask for a snorkel device, said face mask comprising an upper portion and a center portion, and said face mask comprising:

a beam engaged on the upper portion of the face mask and including a middle portion having a cavity formed therein and including two end portions each having an extension extended therefrom for securing to the face mask, a retaining member including an upper leg engaged in said cavity of said beam and including a lower leg having a hook means formed thereon for engaging with the center portion of the face mask so as to be secured onto the face mask, means for securing said upper leg to said beam so as to secure said beam to the face mask, and a light means secured to said beam for lighting purposes.

2. A face mask according to claim 1, wherein said beam includes a pair of lugs extended from said middle portion thereof, a bolt means engaged with said lugs, and said light means includes a housing having a projection extended downward therefrom for engaging with said bolt means so as to be secured to said beam.

3. A face mask according to claim 2, wherein said housing includes a hollow interior and includes at least one battery and a socket engaged in said hollow interior of said housing and includes a lamp means engaged with said socket, and includes a parabolic reflector engaged in said housing, said parabolic reflector includes a center hole for engaging with said lamp means, and said housing includes a switch means engaged therein for controlling said lamp means.

4. A face mask according to claim 1 further comprising a pair of clamping straps secured to said extensions for securing to the face mask so as to secure said beam to the face mask.

* * * * *